(12) United States Patent
Bloom et al.

(10) Patent No.: US 7,695,510 B2
(45) Date of Patent: Apr. 13, 2010

(54) ANNULOPLASTY DEVICE HAVING SHAPE-ADJUSTING TENSION FILAMENTS

(75) Inventors: Eliot Bloom, Hopkington, NH (US); Nasser Rafiee, Andover, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 986 days.

(21) Appl. No.: 11/247,724

(22) Filed: Oct. 11, 2005

(65) Prior Publication Data

US 2007/0083259 A1 Apr. 12, 2007

(51) Int. Cl.
*A61F 2/24* (2006.01)
(52) U.S. Cl. .................................... 623/2.36
(58) Field of Classification Search ............... 623/2.36, 623/2.37
See application file for complete search history.

(56) References Cited

U.S. PATENT DOCUMENTS

| | | | |
|---|---|---|---|
| 2004/0102841 A1* | 5/2004 | Langberg et al. | 623/2.36 |
| 2004/0260393 A1 | 12/2004 | Rahdert et al. | |
| 2005/0004668 A1* | 1/2005 | Aklog et al. | 623/2.36 |
| 2005/0143811 A1* | 6/2005 | Realyvasquez | 623/2.36 |

* cited by examiner

*Primary Examiner*—William H. Matthews
*Assistant Examiner*—Jonathan Stroud

(57) ABSTRACT

A system for treating mitral valve regurgitation includes a tensioning device having a flexible annuloplasty ring, a plurality of anchoring members and a tensioning filament attached to the flexible ring. One embodiment of the invention includes a method for attaching a flexible annuloplasty ring to the annulus of a mitral valve, and adjusting the lengths of segments of the tension filament attached to the flexible ring in order to exert force vectors on the annulus, thereby reshaping the mitral valve annulus so that the anterior and posterior leaflets of the mitral valve close completely during ventricular contraction.

9 Claims, 8 Drawing Sheets

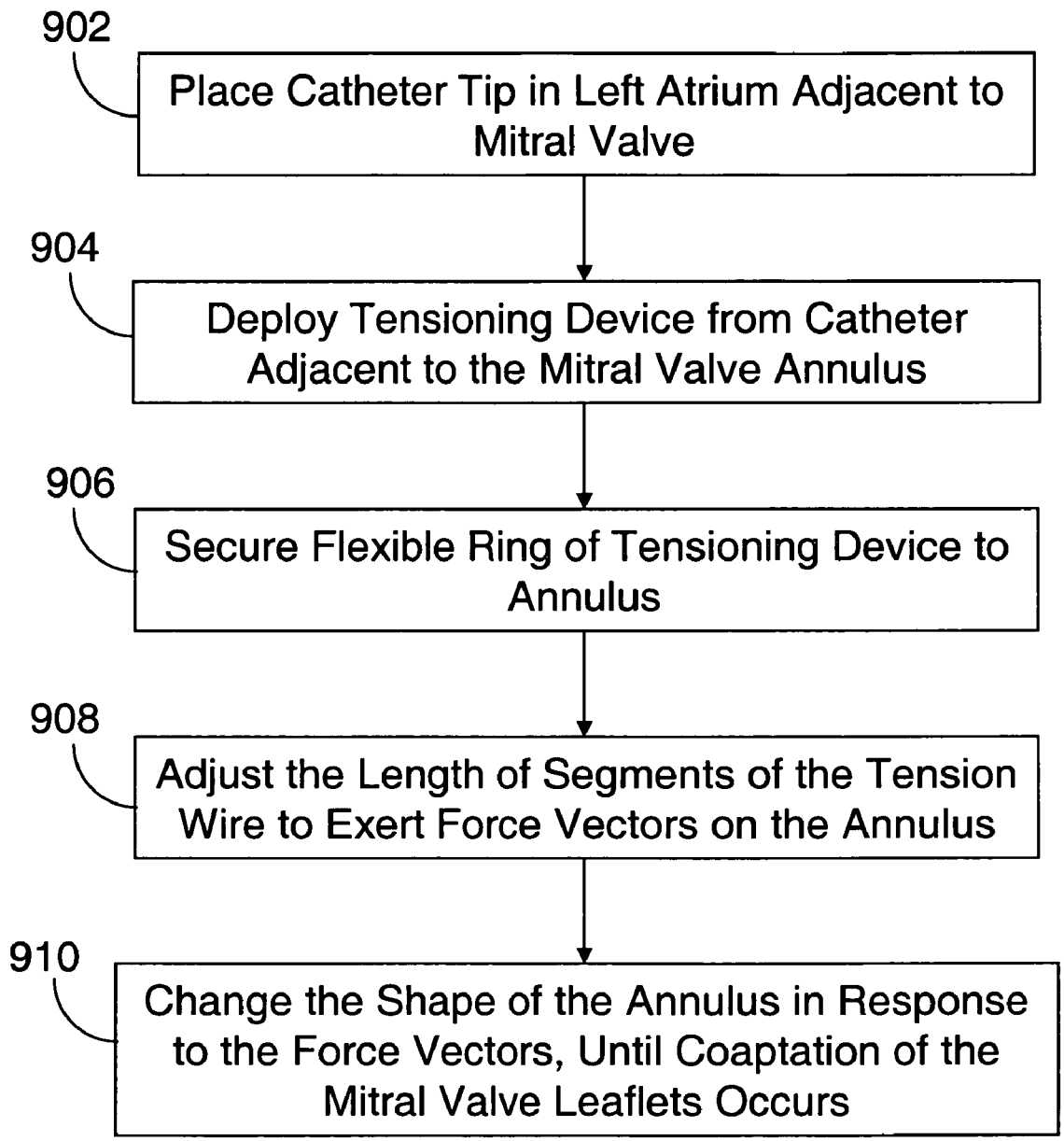

ANNULOPLASTY DEVICE HAVING SHAPE-ADJUSTING TENSION FILAMENTS

FIELD OF THE INVENTION

This invention relates generally to the treatment of mitral valve regurgitation and particularly to a method and device to improve mitral valve coaptation in a diseased heart.

BACKGROUND

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets close during contraction of the left ventricle and prevent blood from flowing back into the left atrium. Due to various cardiac diseases, however, the mitral valve annulus may become distended causing the leaflets to remain partially open during ventricular contraction and thus allow regurgitation of blood into the left atrium. This results in reduced ejection volume from the left ventricle, causing the left ventricle to compensate with a larger stroke volume. However, the increased workload eventually results in dilation and hypertrophy of the left ventricle, further enlarging and distorting the shape of the mitral valve. If left untreated, the condition may result in cardiac insufficiency, ventricular failure, and ultimately death.

It is common medical practice to treat mitral valve regurgitation by either valve replacement or repair. Valve replacement involves an open-heart surgical procedure in which the patient's mitral valve is removed and replaced with an artificial valve. This is a complex, invasive surgical procedure with the potential for many complications and a long recovery period.

Mitral valve repair includes a variety of procedures to repair or reshape the leaflets to improve closure of the valve during ventricular contraction. If the mitral valve annulus has become distended, a frequent repair procedure involves implanting an annuloplasty ring on the mitral valve annulus. The annuloplasty ring generally has a smaller diameter than the annulus, and when sutured to the annulus the annuloplasty ring draws the annulus into a smaller configuration, bringing the mitral valve leaflets closer together, and allowing improved closure during ventricular contraction. Annuloplasty rings may be rigid, flexible or a combination, having both rigid and flexible segments. Rigid annuloplasty rings have the disadvantage of causing the mitral valve annulus to be rigid and unable to flex in response to the contractions of the ventricle, thus inhibiting the normal, three dimensional movement of the mitral valve that is required for it to function optimally. Flexible annuloplasty rings are frequently made of Dacron® fabric and must be sewn to the annular ring with a line of sutures. This eventually leads to scar tissue formation and loss of flexibility and function of the mitral valve. Similarly, combination rings must generally be sutured in place and also cause scar tissue formation and loss of mitral valve flexibility and function.

Another approach to treating mitral valve regurgitation requires a flexible elongated device that is inserted into the coronary sinus and adapts to the shape of the coronary sinus. The device then undergoes a change that causes it to assume a reduced radius of curvature and, as a result, causes the radius of curvature of the coronary sinus and the circumference of the mitral annulus to be reduced. While likely to be effective for modest changes in the size or shape of the mitral annulus, this device may cause significant tissue compression in patients requiring a larger change in the configuration of the mitral annulus. Alternatively, the coronary sinus in a particular individual may not wrap around the heart far enough to allow effective encircling of the mitral valve, making this treatment ineffective. Furthermore, leaving a device in the coronary sinus may result in formation and breaking off of thrombus that may pass into the right atrium, right ventricle, and ultimately the lungs causing a pulmonary embolism. Another disadvantage is that the coronary sinus is typically used for placement of a pacing lead, which may be precluded with the placement of the prosthesis in the coronary sinus.

It would be desirable, therefore to provide a method and device for reducing mitral valve regurgitation that would use minimally invasive surgical techniques, but would overcome the limitations and disadvantages inherent in the devices described above.

BRIEF SUMMARY OF THE INVENTION

One aspect of the invention provides a system for treating mitral valve regurgitation comprising a delivery catheter and a tensioning device. The tensioning device comprises a flexible ring having a plurality of anchoring members and a tensioning filament attached to the flexible ring. The tensioning device is deployed from the catheter adjacent to the mitral valve. The anchoring members are fixed to the annulus of the mitral valve, and the tensioning filament is adjusted so that the shape of the annulus is changed in order to achieve coaptation of the mitral valve leaflets.

Another aspect of the invention provides a method for treating mitral valve regurgitation and includes preloading a tensioning device into an internal lumen of a delivery catheter. The tensioning device comprises a flexible ring, a plurality of anchoring members attached to the flexible ring, and a tensioning filament attached to the flexible ring. The method further comprises deploying the tensioning device from the catheter adjacent to the mitral valve, positioning the flexible ring against the annulus of the mitral valve, and embedding the anchoring members into the annulus. Next, the lengths of segments of the tensioning filament are adjusted, causing the shape of the flexible ring to change. Altering the shape of the flexible ring causes the shape of the annulus to change, thus reducing regurgitation through the mitral valve.

Another aspect of the invention provides a tensioning device for treating mitral valve regurgitation comprising a flexible ring, a plurality of anchoring members attached to the ring, and a tensioning filament, also attached to the flexible ring. Using a catheter, the tensioning device may be deployed proximate the mitral valve. When the anchoring members are fixed to the annulus of the mitral valve and the tensioning filament is adjusted, the shape of the annulus is changed.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

BRIEF DESCRIPTION OF THE FIGURES

FIG. 9 is a flow diagram of a method of treating mitral valve regurgitation in accordance with one aspect of the invention.

DETAILED DESCRIPTION

Throughout this specification, like numbers refer to like structures.

Figure 1:
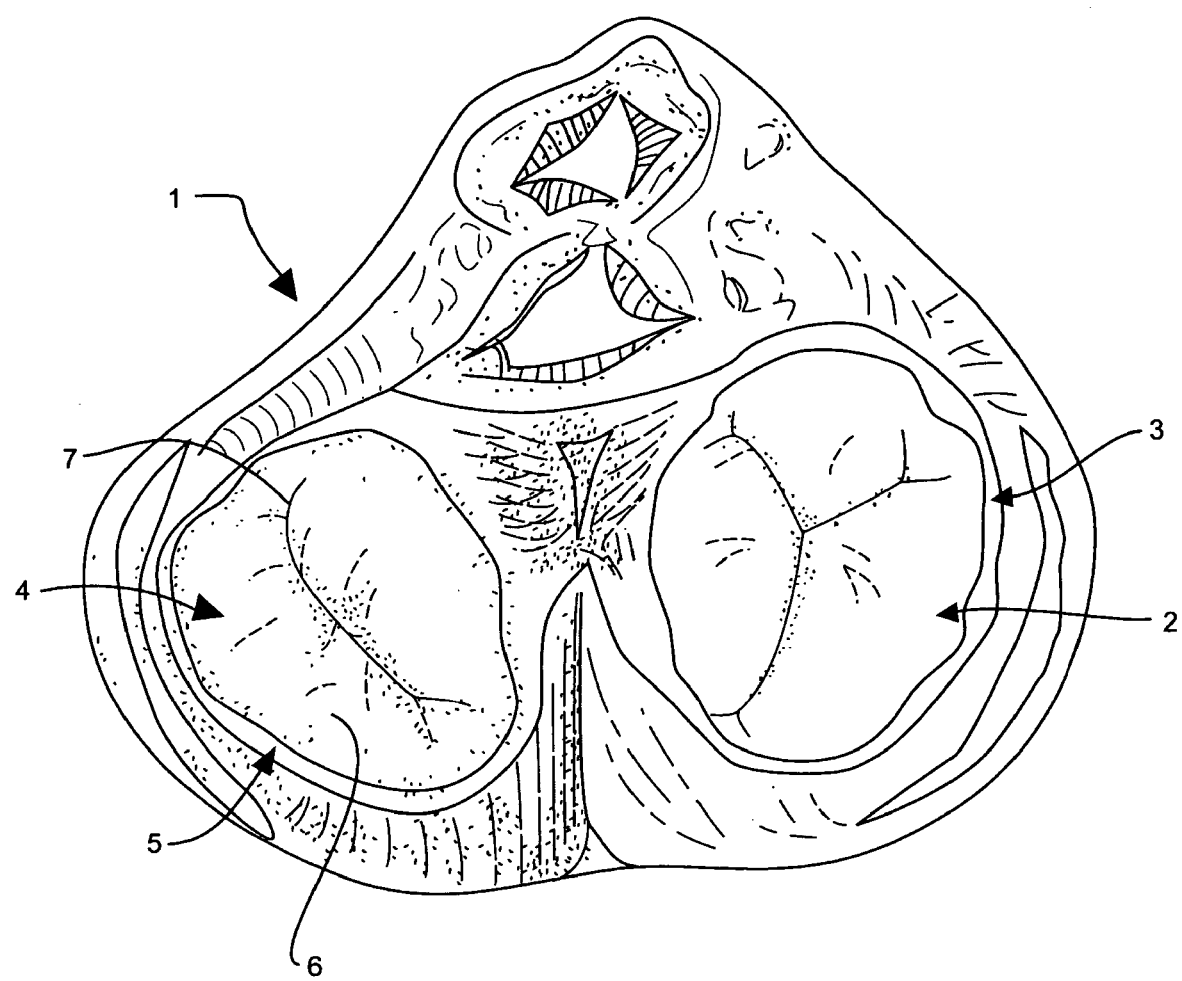
FIG. 1 is a cross sectional schematic view of a heart showing the location of the mitral valve.

Referring to the drawings, FIG. 1 shows a cross-sectional view of heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets.

Figure 2:
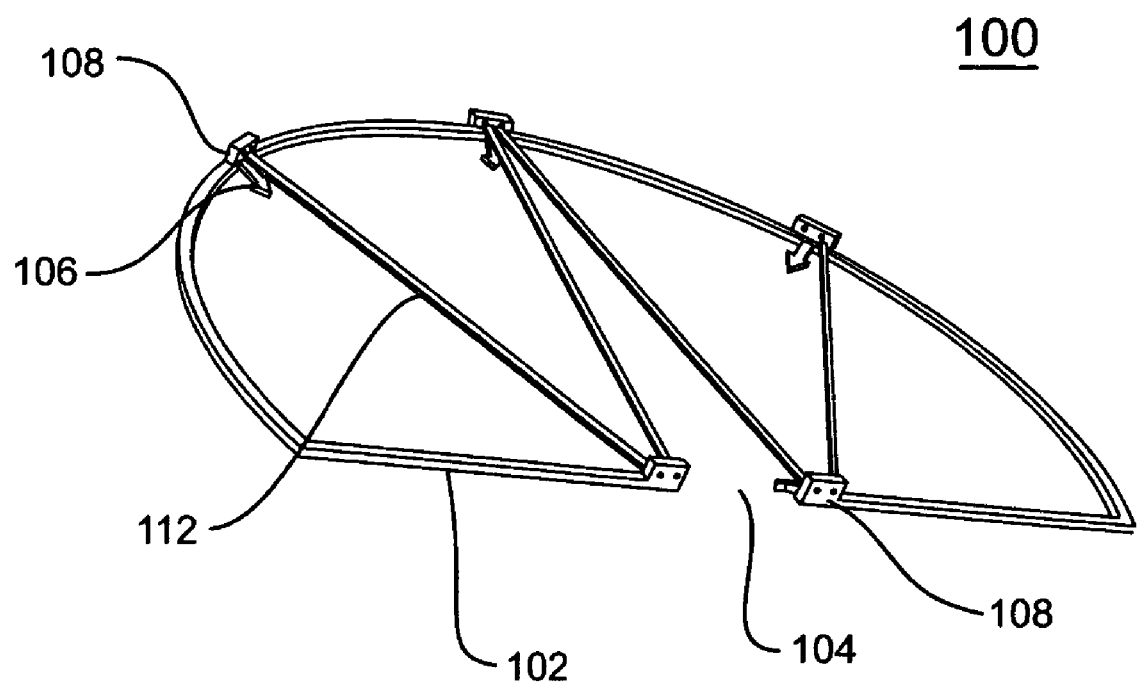
FIG. 2 is a view of the tensioning device having a flexible ring in a D-shaped configuration, in accordance with one aspect of the invention.

Referring to the drawings, FIG. 2 portrays a tensioning device 100 for treating mitral valve regurgitation. Tensioning device 100 includes annuloplasty ring 102. Annuloplasty ring 102 is made of a flexible, biocompatible material that has "shape memory" so that ring 102 can be extended into an elongated configuration and inserted into a delivery catheter, but will re-assume its original shape and dimensions when deployed adjacent to the mitral valve annulus 5. In one embodiment of the invention, flexible ring 102 comprises nitinol, a biocompatible material that gives the ring the needed flexibility and shape memory. Fabrication of annuloplasty ring 102 may include chemical machining, forming or heat setting of nitinol. In addition, the surface of annuloplasty ring 102 should be hemocompatible, and cause minimal blood clotting or hemolysis when exposed to flowing blood. In one embodiment of the invention, annuloplasty ring 102 comprises a flexible, nitinol ring with a Dacron® cover. Dacron®, a polyester fiber (E.I. Du Pont De Nemours & CO., Inc.) is a material known in the art to have the necessary hemocompatible properties and may be used in the cardiovascular system.

The size and shape of annuloplasty ring 102 are selected to fit the configuration of the mitral valve annulus 5. In one embodiment of the invention, the annuloplasty ring 102 is shaped like the letter D, and has a small gap 104 in the straight portion.

A plurality of anchoring members 106 are disposed about flexible annuloplasty ring 102 and are used to attach annuloplasty ring 102 to the mitral valve annulus. In one embodiment of the invention, anchoring members 106 are barbs or prongs, and are formed as part of flexible D-shaped ring 102. Anchoring members 106 are oriented at an angle of 10-45 degrees in relation to the plane of flexible ring 102 so that they will embed in the annulus when ring 102 is positioned against the surface of the mitral valve annulus.

Figure 3:
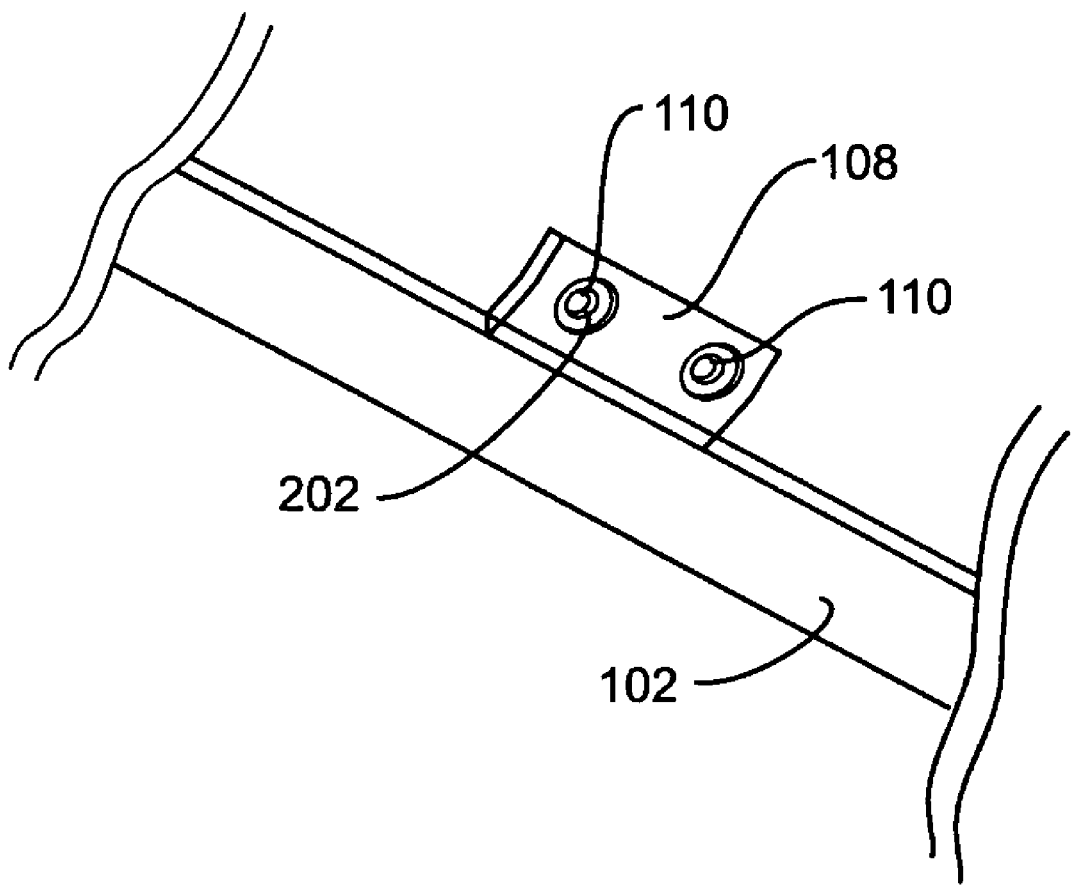
FIG. 3 shows a cleat portion of the tensioning device, in accordance with one aspect of the invention.

A plurality of cleats 108 is disposed about flexible ring 102. Each cleat is paired with an anchoring member 106 and each cleat/anchoring member pair is located at the same planar point of flexible ring 102. In one embodiment of the invention, cleats 108 are formed as part of flexible D-shaped ring 102. Each cleat 108 has either one or two through holes 110 there through (FIG. 3). Holes 110 may be approximately 0.05 to 0.2 mm in diameter and may be counter-bored. Filament 112 is laced through holes 110 and spans flexible ring 102. Filament 112 may be made of metal wire or polymer, and may be a monofilament or a twisted or braided fiber. Holes 110 allow filament 112 to be adjusted to change the length of the segment of filament 112 spanning flexible ring 102 between each pair of cleats 108. Each segment of filament 112 may be adjusted by pulling on filament 112 at the outside edge of cleat 108 at the end of that segment of filament 112, and drawing it through the adjacent hole 110. Once filament 112 is moved through selected hole 110 in one direction, flexible lip 202 surrounding selected hole 110 grips filament 112 and prevents it from moving. Thus, each segment of filament 112 spanning the flexible ring 102 may be adjusted individually and placed under a different amount of tension. As each segment of filament 112 is adjusted, force vectors resulting from the pull on two adjacent segments of filament 112 are exerted on flexible ring 102, and cause the shape of flexible ring 102 to change. The direction and magnitude of the force vectors exerted at each cleat 108 are determined by adjusting the segment of filament 112 that extends through each cleat 108. Because flexible ring 102 is fastened to the annulus of the mitral valve, the annulus is drawn into a configuration similar to that of flexible ring 102. Consequently, the shape of the mitral valve annulus is altered by the force vectors exerted at each cleat 108 on both flexible ring 102 and the annulus. The force vectors are selected to change the configuration of the annulus as needed in order to achieve coaptation of the mitral valve leaflets.

Figure 4:
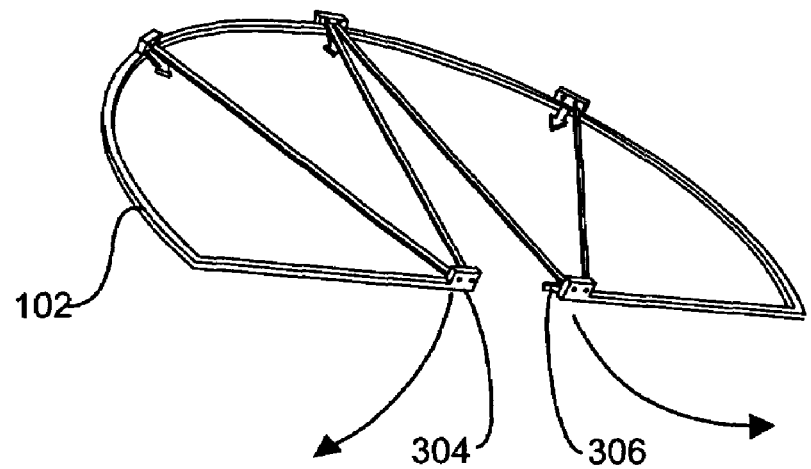
FIG. 4 portrays the flexible ring of the tensioning device in a D-shaped configuration, in accordance with one aspect of the invention.
Figure 5:
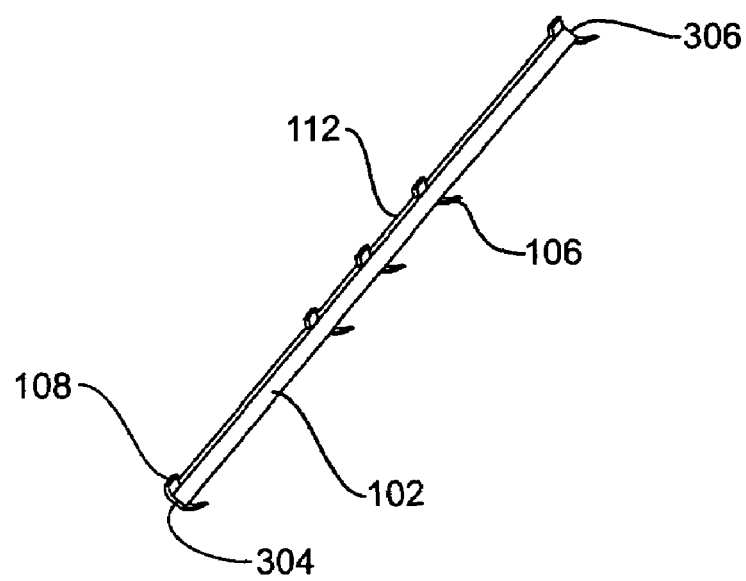
FIG. 5 portrays the flexible ring of the tensioning device in an elongated configuration, in accordance with one aspect of the invention.

Flexible ring 102 can be transformed from its D-shaped configuration (FIG. 4) into an elongated, linear configuration (FIG. 5). The two ends 304, 306 of flexible ring 102 may be moved in opposite directions until tensioning device 100 is in an elongated, essentially linear shape. Because flexible ring 102 comprises a shape memory material such as nitinol, tensioning device 100 will spontaneously revert to an unconstrained, D-shaped ring configuration when free to do so.

Figure 6:
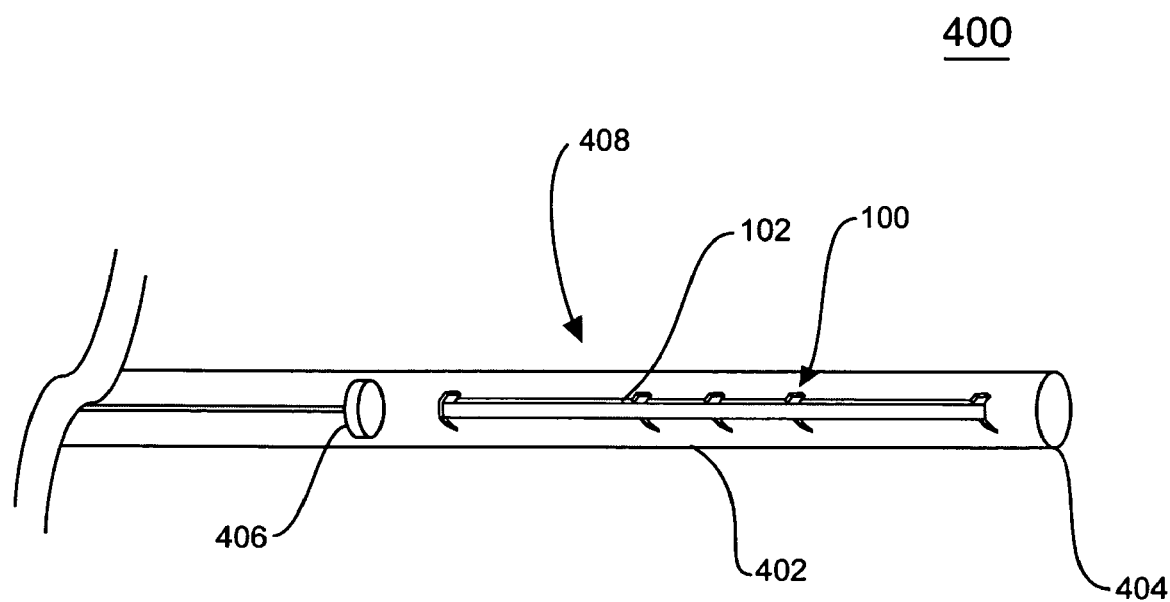
FIG. 6 is a side view of a tensioning device in an elongated configuration inside the distal portion of a delivery catheter, in accordance with one aspect of the invention.

FIG. 6 is a side view of the distal portion of system 400 for treating mitral valve regurgitation using minimally invasive surgical techniques. Flexible tensioning device 100 is contained within a sheath 402 forming the distal portion of delivery catheter 408. In one embodiment of the invention, delivery catheter 402 is flexible and configured so that it can be inserted into the cardiovascular system of a patient. Such catheters are well known in the art and typically are approximately 12 French in diameter, and are made of flexible, biocompatible polymeric materials such as polyurethane, polyethylene, nylon and polytetrafluoroethylene (PTFE). Flexible annuloplasty ring 102 of tensioning device 100 is opened to its elongated configuration (FIG. 5), and placed within the lumen of catheter 408 near catheter distal end 404. Within the lumen of catheter 408, and proximal to tensioning device 100 is a deployment device, such as flexible rod 406 that is used to deploy tensioning device 100 by pushing it from catheter distal tip 404. After tensioning device 100 is deployed, flexible rod 406 may be withdrawn from catheter 408. In one embodiment of the invention, the interior surface of catheter 408 is coated with a lubricious material such as silicone, polytetrafluroethylene (PTFE), or a hydrophilic coating. The lubricious interior surface of catheter 408 facilitates the longitudinal movement of flexible rod 406 and deployment of tensioning device 100.

To deliver tensioning device 100 adjacent to the mitral valve (FIG. 7), transeptal wall 504 between right atrium 502 and left atrium 506 is perforated according to well-established techniques. Delivery catheter 400 containing tensioning device 100 may be inserted into the subclavian vein, through the superior vena cava, and into right atrium 502. Then, the distal end of delivery catheter 400 is advanced through the septal perforation, into left atrium 506 and placed in proximity to annulus 510 of mitral valve 508. In one embodiment of the invention, the placement procedure is performed using fluoroscopic or echocardiographic guidance.

Figure 7:
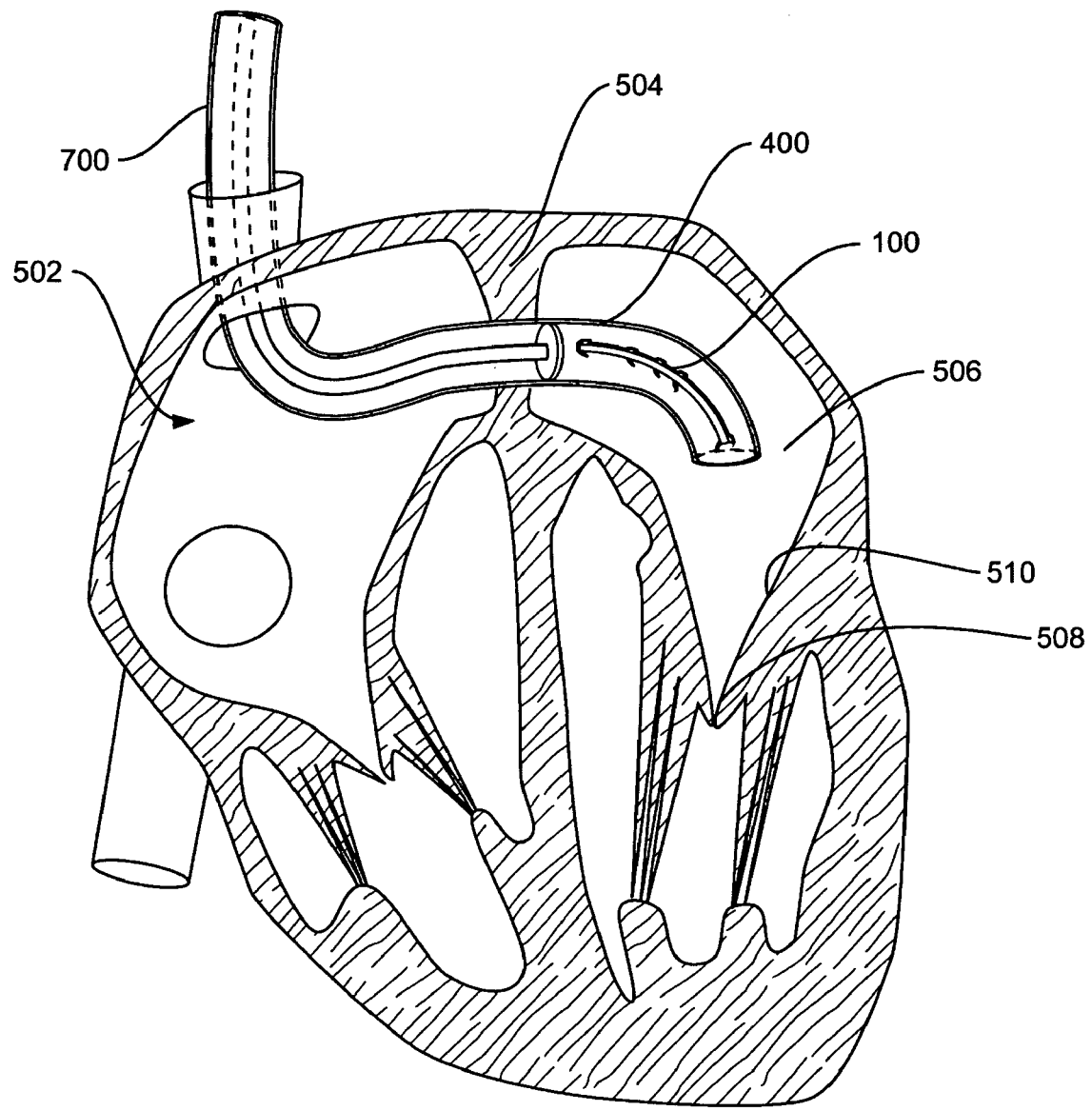
FIG. 7 is a schematic view illustrating the placement of the tensioning device adjacent to the mitral valve, in accordance with one aspect of the invention.

FIG. 9 is a flowchart illustrating method 900 for treating mitral valve regurgitation, in accordance with one aspect of the invention. The distal tip of a delivery catheter containing the flexible annuloplasty ring is placed in the left atrium adjacent to the mitral valve (Block 902). As shown in FIG. 7, the catheter 700 is inserted into the vascular system of the patient, through the right atrium, and into the left atrium, adjacent to the mitral valve annulus. Next, the tensioning device is deployed from the catheter (Block 904). The flexible tip of the delivery catheter is moved along the surface of the annular ring, and used to direct the placement of the tensioning device. At the same time, a deployment device, such as a flexible rod within the catheter is used to deploy the ring by pushing it from the distal tip of the catheter and laying the flexible ring along the mitral valve annulus. The D-shaped ring is positioned so that the straight portion is disposed on the posterior annulus. The tensioning device will automatically assume a D-shaped configuration when it is pushed from the catheter, and lays on the surface of the annulus, with the barbs against the surface of the annulus. In one embodiment of the invention, an inflatable balloon is then extended from the distal tip of the delivery catheter immediately adjacent to the top of the D-shaped ring. The balloon is inflated to push the flexible ring against the annular surface, causing the barbs to be embedded in the valve annulus and anchor the tensioning device in place (Block 906).

Figure 8:
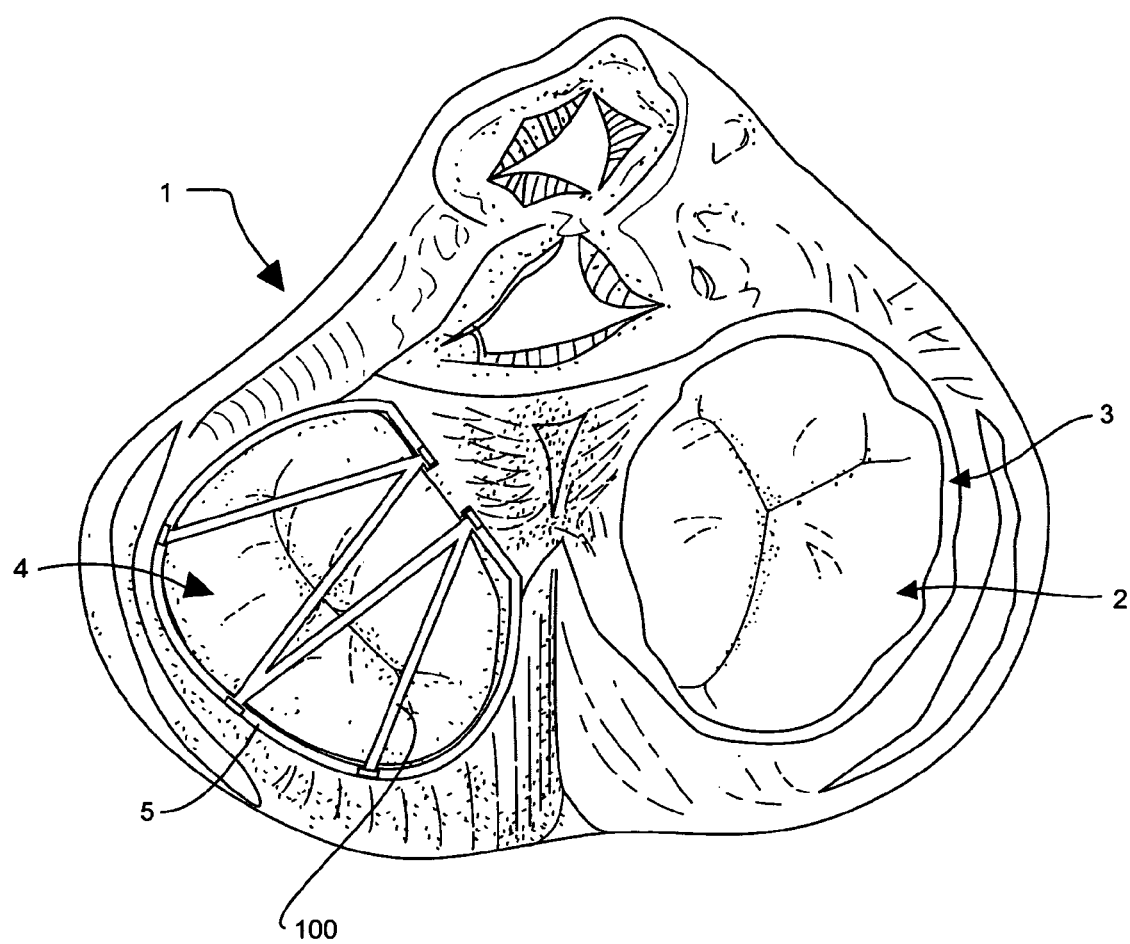
FIG. 8 is a schematic view illustrating the tensioning device placed adjacent to the mitral valve, in accordance with one aspect of the invention.

Once the flexible ring is secured to the valve annulus by the anchoring barbs, the length of each segment of the tension filament that spans the flexible ring is adjusted so that force vectors are exerted on the mitral valve annulus (Block 908). In one embodiment of the invention, the flexible rod used to deploy the tensioning device is withdrawn from the catheter, forceps are advanced through the catheter and the tip of the forceps is placed adjacent the mitral valve annulus. Next, each segment of the tensioning filament is adjusted by using the forceps to grasp the filament at the cleat surface facing the outside of the ring at the ends of the filament segment that is to be adjusted. The filament is then pulled through the hole in that cleat. When released, the newly adjusted length of each filament segment is fixed in place by the inner lip of the hole(s) through the cleat at each end of the segment. Because the flexible ring is securely fastened to the annular ring of the mitral valve, the shape and diameter of the annular ring will also be changed by the force vectors exerted on it (Block 910). The magnitude and direction of the force vectors can be selected so that force is exerted on the valve annulus only where it is needed to reshape the mitral valve annulus so that the anterior and posterior leaflets close during ventricular contraction. Improvement in the valve closure can be evaluated by checking for decreased pressure in the left atrium. Finally, the delivery catheter is withdrawn from the body of the patient. FIG. 8 illustrates a schematic view of the tensioning device 100 placed adjacent to the mitral valve in accordance with method 900.

While the invention has been described with reference to particular embodiments, it will be understood by one skilled in the art that variations and modifications may be made in form and detail without departing from the spirit and scope of the invention.

What is claimed is:

1. A system for treating mitral valve regurgitation comprising:
   a catheter;
   a tensioning device received in a lumen of the catheter, the tensioning device including a flexible ring,
   a plurality of anchoring members disposed about the flexible ring,
   a plurality of cleats disposed about the flexible ring wherein each cleat is paired with an anchoring member and each cleat/anchor pair is located at the same planar point on the flexible ring; and
   a tensioning filament slidably attached to the cleats disposed on the flexible ring, wherein the tensioning member is attached to span between opposing cleats;
   wherein when the system is delivered proximate a mitral valve, the tensioning device is deployed, the anchoring members are fixed to an annulus of the mitral valve and the tensioning filament is adjusted to change the shape of the annulus.

2. The system of claim 1 wherein in the flexible ring has a D-shaped planar configuration and an elongated configuration.

3. The system of claim 1 wherein the anchoring members comprise barbs positioned at an angle to the plane of the flexible ring.

4. The system of claim 3 wherein the barbs embed into the mitral valve annulus and maintain the flexible ring in a supra-annular position adjacent to the mitral valve annulus.

5. The system of claim 1 wherein the tensioning filament is slidably attached to each cleat.

6. The system of claim 5 wherein the tensioning filament is attached to each cleat though a double counter bored hole, wherein the double counter bored hole includes a flexible lip, the flexible lip surrounding the double counter bored hole and configured to grip the tensioning filament and prevent movement of the tensioning filament.

7. The system of claim 5 wherein, when the tensioning filament is adjusted at each cleat, force vectors are exerted on the mitral valve annulus and cause the shape of the mitral valve annulus to change.

8. The system of claim 1 wherein the delivery catheter comprises:

an outer sheath;
a delivery chamber within the sheath at a distal end of the catheter; and a deployment device positioned within the sheath, wherein when the system is delivered adjacent to a mitral valve, the flexible ring is deployed from the delivery chamber and positioned adjacent to the annulus of the mitral valve.

9. The system of claim 8 further comprising an inflatable balloon at the distal tip of the catheter wherein, when the balloon is inflated, the flexible ring is seated against the annulus of the mitral valve.

* * * * *